United States Patent [19]

Helfrich et al.

[11] Patent Number: 5,423,231
[45] Date of Patent: Jun. 13, 1995

[54] FOOT CONTROL MECHANISM FOR A DENTAL APPARATUS

[75] Inventors: Hans Helfrich, Mannheim; Hermann Landgraf, Lorsch; Josef Hain, Laudenbach, all of Germany

[73] Assignee: Siemens Aktiengesellschaft, Munich, Germany

[21] Appl. No.: 53,420

[22] Filed: Apr. 28, 1993

[30] Foreign Application Priority Data

May 18, 1992 [DE] Germany .......... 42 16 371.4
May 18, 1992 [DE] Germany .......... 42 16 370.6

[51] Int. Cl.⁶ .......... G05G 1/14; A61C 1/02; H01H 3/14
[52] U.S. Cl. .......... 74/561; 74/560; 74/512; 433/101; 200/86.5
[58] Field of Search .......... 74/512, 560, 561, 562; 433/101; 200/86.5

[56] References Cited

U.S. PATENT DOCUMENTS

| | | | |
|---|---|---|---|
| 2,762,891 | 9/1956 | Hill et al. | 201/48 |
| 2,857,493 | 10/1958 | Tascher | 200/86.5 |
| 2,866,024 | 12/1958 | Ginn | 200/86.5 |
| 2,872,542 | 2/1959 | Thompson | 200/86.5 |
| 2,878,336 | 3/1959 | Ehrlich | 200/86.5 |
| 3,983,344 | 9/1976 | Straihammer | 74/560 X |
| 4,172,217 | 10/1979 | Miller | 200/86.5 |
| 4,354,838 | 10/1982 | Hoyer et al. | 433/101 |
| 4,403,123 | 9/1983 | Shek | 200/86.5 X |
| 4,417,875 | 11/1983 | Matsui | 200/86.5 X |
| 4,523,911 | 6/1985 | Braetsch et al. | 433/101 |
| 4,798,535 | 1/1989 | Nielsen | 433/101 |

FOREIGN PATENT DOCUMENTS

| | | | |
|---|---|---|---|
| 0455852 | 11/1991 | European Pat. Off. | 74/560 |
| 14028 | 9/1956 | Germany | 200/86.5 |
| 2231265 | 10/1974 | Germany | 200/86.5 |
| 2814869 | 10/1979 | Germany | 200/86.5 |

*Primary Examiner*—Vinh T. Luong
*Attorney, Agent, or Firm*—Hill, Steadman & Simpson

[57] ABSTRACT

A foot control mechanism for a dental apparatus has a tiltable actuation member mounted on a base part and an arrangement for holding the tiltable actuation member in a neutral position, which requires sufficient force to move the actuation member in either direction from the neutral position to a switch position. To accomplish this, the structure includes a mounting arrangement utilizing a pair of spaced-apart bearings extending parallel to each other which bearings receive projections on the other element and, preferably, a catch member is provided which provides a resistant force from movement from the neutral position.

16 Claims, 4 Drawing Sheets

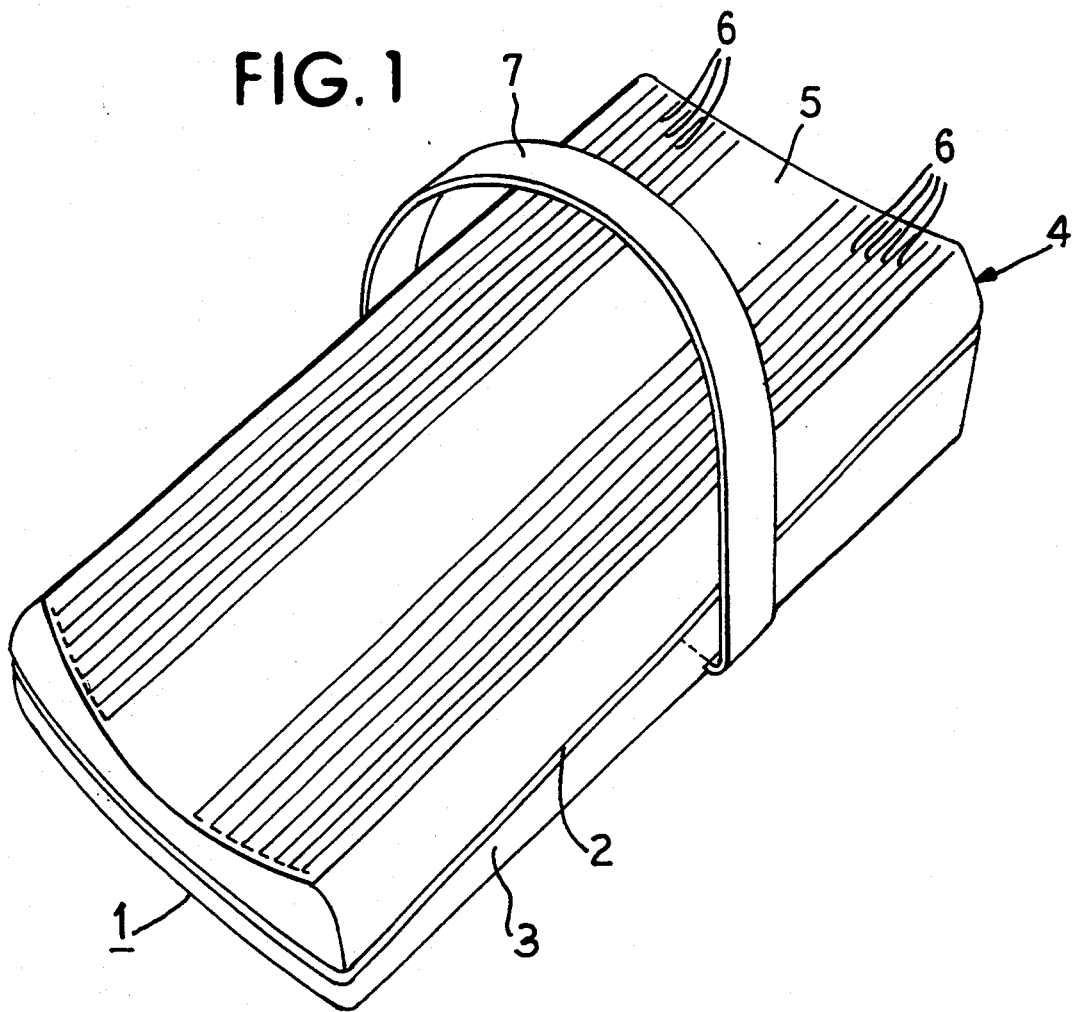

FOOT CONTROL MECHANISM FOR A DENTAL APPARATUS

BACKGROUND OF THE INVENTION

The present invention is directed to a foot control mechanism for a dental apparatus, wherein an essentially plate-shaped and horizontally-aligned actuation member is present on which the foot of an operator can be placed overall and that, for triggering a switch or control function, the member can be brought from a neutral position into at least two different switching positions directly opposite from one another.

Pending U.S. application Ser. No. 07/694,634, which issued as U.S. Pat. No. 5,300,926 on Apr. 5, 1994 and claims priority from European Application 90108740.3 that was published as European Published Application 0 455 852, discloses a foot control mechanism wherein the pedal or foot support pivots or rotates around a horizontal axis and also can be pivoted or rotated around a vertical axis extending perpendicular to the horizontal axis. Although this type of foot control mechanism has certain advantages over other foot control mechanisms, whose pivot points lie in the region of the tip of the toes or the heel, a holding of the foot support or pedal in a neutral, quiescent position represents a certain problem area, because holding of the pedal in this neutral position can only be accomplished by the user exercising care and muscle control. The operator's foot must always be positioned in a beneficial position over the rotational axis and must also be held in this position during operation in order to always assure a more or less relaxed foot position. Variable heel stops or detents would also have to be provided in order to take into consideration different shoe sizes for the operator. These variable heel stops, however, would deteriorate from the manipulability and the ease of operation.

U.S. Pat. No. 2,762,891, whose disclosure is incorporated herein by reference thereto, discloses a foot switch that contains an actuation element that is fashioned as a pedal and is obliquely placed in the initial position. The pedal on which the foot of the operator can be planarly placed has a seating part in the region of the heel that is intended to lend the foot a reliable held. The pedal is pressed against the detent in an obliquely residing initial position on the basis of an approximately centrally placed compression spring. The pedal can, thus, be tilted around a horizontal axis approximately placed in the lower third of the length of the foot switch and close to the heel. Thus, the pedal is capable of being tilted opposite the force of the compression spring until the additional stop or detent is reached. In its upper third, the pedal contains a roller level that can roll on a curved path or cam that proceeds concentrically relative to the midpoint of the housing of the foot switch. The cam is secured to a part mounted for rotation on a vertical axis, which is, in turn, coupled to a potentiometer for varying the speed of the dental motor. A swivel motion of the above-mentioned swivellable part is initiated with the tilting of the actuation element and, thus, an adjustment of the potentiometer is achieved. This device would enable having a control of the speed of a motor in one direction and also a control of the speed in the opposite direction.

In this known foot switch, the pedal cannot be brought from a neutral position into two operating positions that are opposite to one another. It can merely be moved from one final position in one direction until the second final position is reached.

SUMMARY OF THE INVENTION

The object of the present invention is to provide a foot control mechanism with which the above-mentioned disadvantages can be avoided.

To accomplish these goals, the present invention is directed to a foot control mechanism for a dental apparatus, wherein an actuation member is mounted by means for mounting the actuation member to be tiltable on a base part and the foot of the operator is placed all over this actuation member, which can be brought from a neutral position into at least two switch positions directly opposite one another for triggering a switch/control function with at least one of the switch/control elements being actuated in the switch position, wherein the actuation member is seated on the base part with the assistance of two spaced bearing arrangements, which are part of the means for mounting are arranged at a spacing from one another and with their axis extending parallel to one another.

Since the actuation member is seated on the two bearing arrangements at a distance from one another, the neutral or quiescent position can be maintained in a broad range independent of the position and also independent of the shoe size of the operator without the foot having to be held rigidly in a very specific position. The actuation can also occur under a great load with little exertion of force and a reliably seated foot position. Particular advantages occur when a switch plate is tiltably seated with the assistance of a leaf spring, because an easy assembly and disassembly of the foot control mechanism can then be accomplished with the assistance of simple, cost-beneficial component parts. Another advantage is that such leaf springs enable an extremely good compensation for tolerances.

The measure proposed according to the advantages of the present invention are that the actuation member is held in a neutral position by detent means for providing a defined retaining force. The detent means includes catch elements and the actuating member is limited by stops after a relatively short displacement path, and the control elements triggered after the pressure point defined by the retaining force of the detent means is overcome and allows a facilitated operation with an improved reliability with respect to the actuation of the switch and/or control element for triggering a control event to be achieved. This, thus, proceeds in the perception that a certain muscle exertion is required for overcoming the neutral position loaded with a definite retaining force or pressure point of the detent means. After overcoming this retaining force, this muscle exertion leads to an excess stroke that is intercepted in combination with the stops allocated to the switch position, as a result whereof the operator receives a clearly noticeable answerback or feedback that the neutral position has been left and that the switch event has been triggered. The answerback about the switch condition can particularly be clearly noticed by the operator, because of the limitation of the excess stroke by the stops occurs after a relatively short displacement path immediately after overcoming the pressure point.

Other advantages and features of the invention will be readily apparent from the following description of the preferred embodiments, the drawings and claims.

BRIEF DESCRIPTION OF THE DRAWINGS

FIG. 1 is a perspective view of a foot control mechanism in accordance with the present invention;

DESCRIPTION OF THE PREFERRED EMBODIMENTS

Figure 2A:
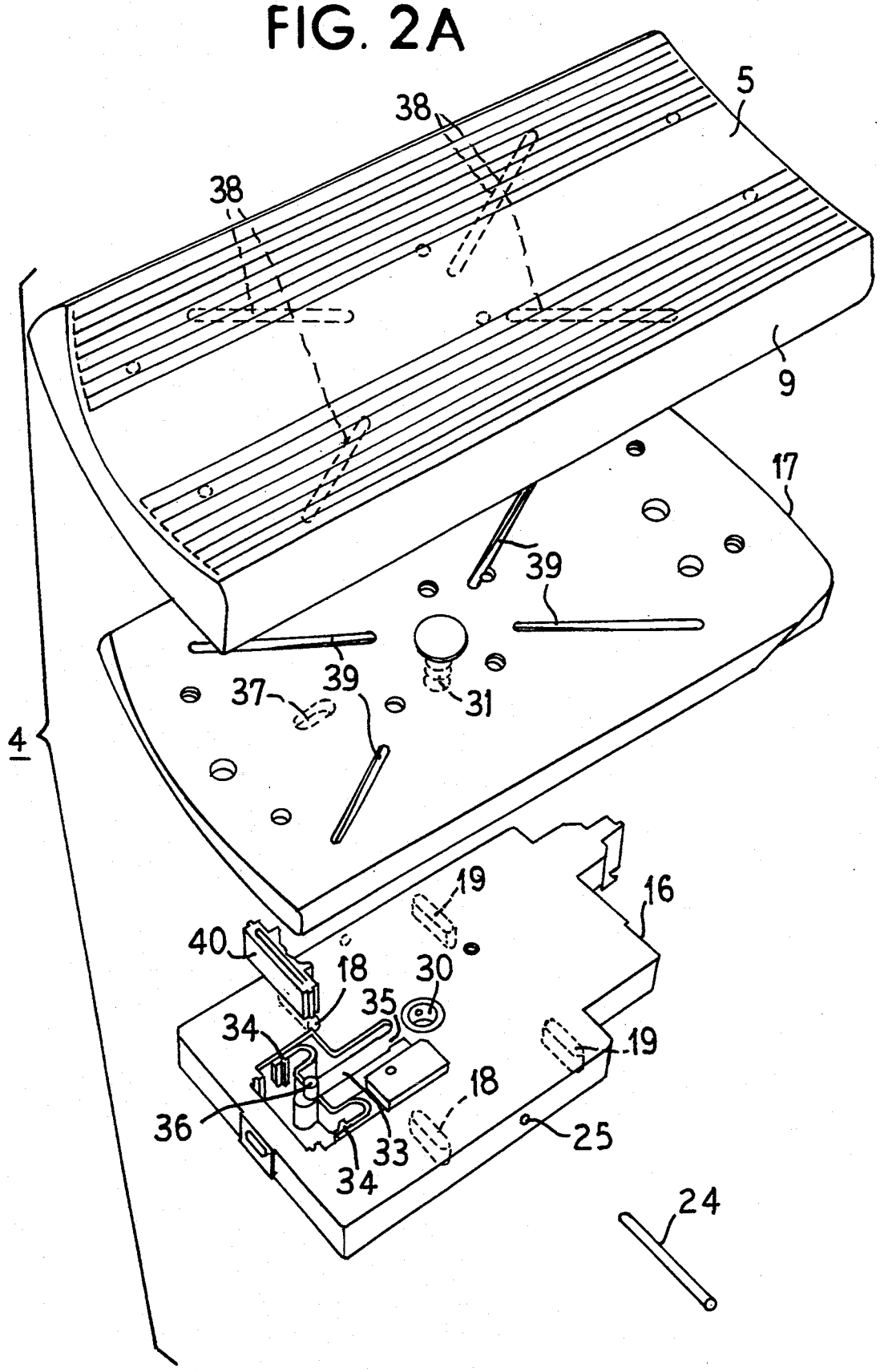
FIG. 2A is an exploded view of an upper part of the foot control mechanism of the present invention.

The principles of the present invention are particularly useful in a foot control mechanism illustrated in FIG. 1, which has a housing 1 that is essentially rectangular in the plan view and is divided into two housing halves by being longitudinally divided along a parting line 2 into a base part 3 and into an actuation which is generally indicated at 4 and member is arranged above the base part 3. The actuation member 4 contains a bearing or foot support 5 fashioned in a hood-like manner that has a slightly concave surface in cross section and which proceeds from a neutral or middle portion to lateral sections that contain a plurality of longitudinally extending seating surfaces formed by ridges or grooves 6 that are graduated in a sawtooth manner. The longitudinally proceeding edges formed by these ridges lend the operator's foot a good hold, particularly given lateral excursion motions, as a result whereof tilting and-/or rotary motions can be exactly carried out. Changing the position at which the foot control mechanism is erected can be unproblematically implemented with the assistance of a shackle 7 that is preferably detachably secured to the base part 3.

Figure 2B:
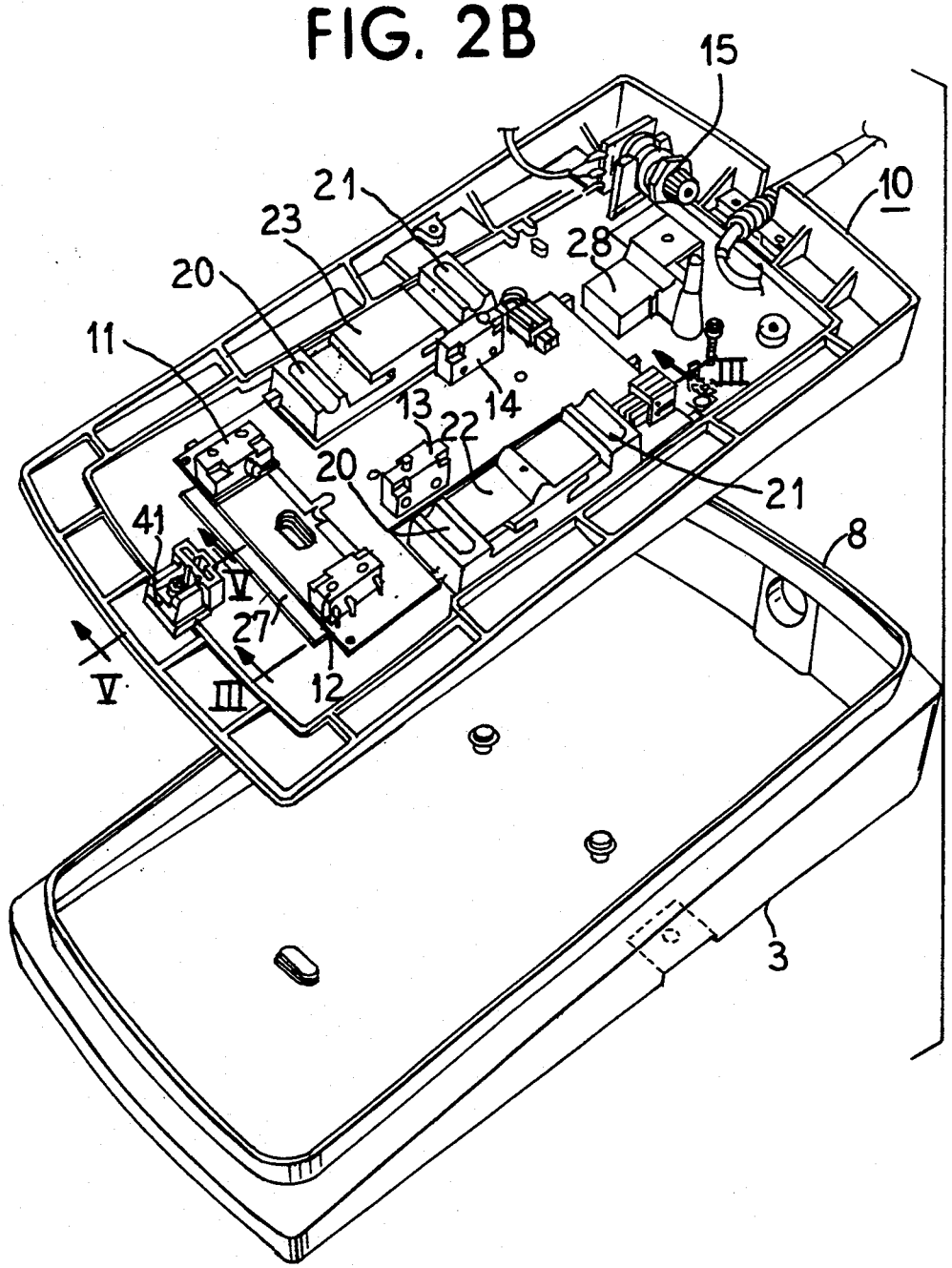
FIG. 2B is an exploded view of the lower or base part of the foot control mechanism.

As illustrated in FIG. 2B, the base part 3 is constructed trough-like and contains a drawn-up and slightly outwardly-arced edge 8 that corresponds to a slightly inwardly-drawn edge 9 of a foot support part 5, which is constructed in a hood-like fashion as illustrated in FIG. 2A. In the assembled condition, a connection that is protected against splashes and liquid is produced by the edge 9 telescopically receiving the flange or edge 8. Both the base part 3 as well as the foot support 5 are composed of an elastic material, preferably of rubber, and as a result of this material, an unproblematical switching both when tilting around a transverse axis, as well as rotating around a horizontal axis, is possible, as proceeds in greater detail from the following description.

As illustrated in FIG. 2B, a base plate 10 of solid material, preferably aluminum, can be introduced into the base part 3, which is fashioned with a recess for receiving the part 10. The base plate 10 is the carrier of a plurality of control switch elements 11–15, as well as electrical terminal elements that are not referenced in detail. The control elements, such as 11, 12, 13 and 14 can be microswitches, whereas the control element 15 is a speed control element. The switch and control elements 11–15 are actuated with a switch plate 16 (FIG. 2A), which is arranged above the base plate 10 when in the assembled condition and is attached to a pedal 17 which is arranged thereabove that, in turn, is connected to the foot support part 5. The bearing of the switch plate 16 on the base plate 10 is set forth in greater detail with reference to the schematic illustration of FIG. 3A.

Figure 3A:
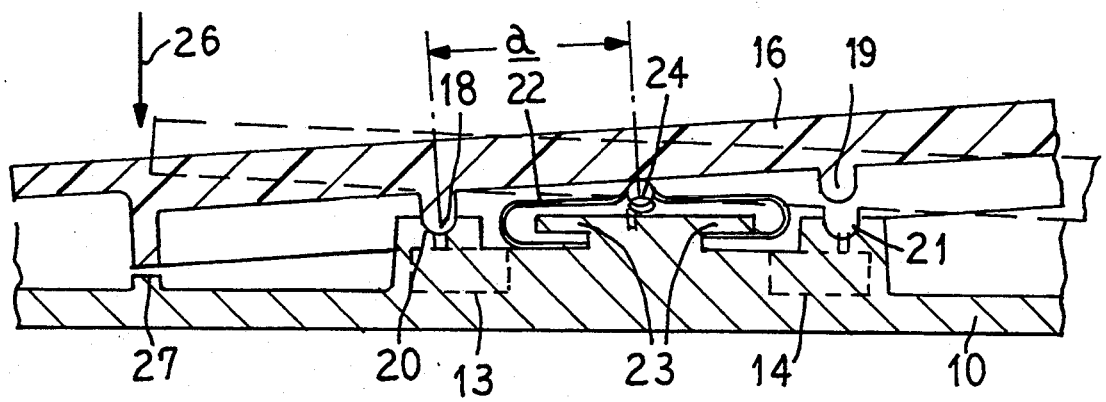
FIG. 3A is a partial longitudinal cross sectional view taken approximately along line III—111 of FIG. 2B; and of the bearing arrangement and a stop for tilting the upper part around a horizontal axis to one of the switching positions from a neutral position shown in broken lines.

The underside of the switch plate 16 has two pair of projections 18 and 19, which, as illustrated in FIG. 3A, have semi-circular cross sections. The base plate 10 has two half-shell bearing seats or bearing parts 20 and 21 which have a corresponding semicircular groove. In a neutral position or quiescent position (shown in broken lines in FIG. 3A), the four projections 18, 19 are held without play in the half-shell radial bearings 20 and 21 with the assistance of two leaf springs 22, of which only one on the right side is illustrated in FIG. 2B. In this position, the control elements 13 and 14 arranged under the projections 18, 19 and adjusted in the plane of the bearing shells have their actuation elements pressed.

The leaf springs 22 are fashioned clasp-like and embrace, first, a projection 23 of the base plate 10 and, second, a fall floating axle 24 arranged at both sides that are guided in corresponding bores 25 of the switch plate 16, as illustrated in FIG. 2A. Thus, the means for mounting the actuation member includes the two pairs of projections 18, 19, the bearing seats 20 and 21, the two leaf springs 22 and the floating axle 24 of the switch plate 16. The projection and bearing arrangements or combinations 18 and 20 and 19 and 21 formed in this way have a distance from one another that corresponds to twice the distance a of the full floating axle position from either of the axes of the bearings 20 or 21. In the present exemplary embodiment, the spacing a amounts to approximately 20 mm through 30 mm, given an overall length of approximately 200 mm through 250 mm for the pedal and an overall width of approximately 100 mm through 140 mm.

Figure 3B:
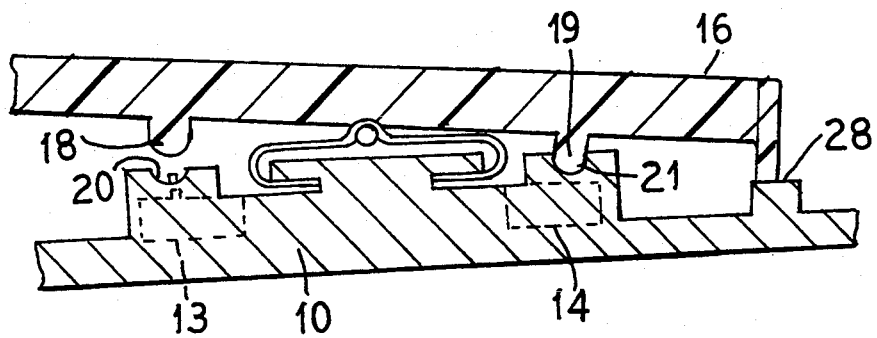
FIG. 3B is partial cross sectional view similar to FIG. 3A showing the upper part tilted to the other and opposite switching position.

When the switch plate is pressed in the direction of the arrow 26 of FIG. 3A, then the switch plate does not swivel around the full floating bearing or axle 24, but around the projection 18 and bearing 20. The two projections 19 are then lifted from their half-shell bearings 21. The actuation element of the control element 14 lying next to bearing 21 is, thus, relieved and a switch or, respectively, control signal is thereby triggered. Advantages of this arrangement are good adjustment of the control elements and the creation of exact turn-on and turn-off points. After a tilting motion having a relatively short stroke of approximately 1 mm through 2 mm adjustment path, the switch plate 16 will press against a stop or detent 27 of the base plate 10. An analogous case applies to a movement of the pedal in an opposite direction, wherein a stop or detent 28 (FIG. 2B) limits the tilt motion of the switch plate in the other direction (see FIG. 3B). When tilted or pivoted in the other direction, the switch 13 will be disengaged. The switch elements 13, 14 and 15, which are not activated in the quiescent or neutral position, are then activated in the switch positions limited by either the stop 27 or the stop 28 and either the switch element 13 is actuated or the switch elements 14 and 15 are actuated, depending on the direction of rotation of the switch plate. The switch elements 13 and 14 are arranged laterally offset, as viewed in the longitudinal direction, and switching errors can be largely avoided on the basis of this arrangement.

As illustrated in FIG. 2A, the switch plate 16 contains a bore 30 which receives a male member 31 of the pedal 17 when in the assembled position. The pedal 17 can be pivoted relative to the switch plate 16 around this axis and moves in a substantially horizontal plane around the vertical axis formed by the pin 31. The switch plate 16 also contains an applied spring beam 33, which is constructed to be approximately T-shaped, and has actuating areas 34 on both ends of the transverse leg for the actuation of the switch elements 11 and 12 of FIG. 2B. As a result of its elasticity, the spring beam 33 can be deflected toward either side around a pivot point that lies approximately at a position 35. A dog peg 36, which is centrally located on the spring beam 33, engages into a corresponding dog bore, groove or slot 37 of the pedal 17 so that the spring beam 33 is correspondingly deflected around the swivel axis 35 when the pedal is turned or rotated around the bearing member 31.

A connection of the foot support 5 to the pedal 17 occurs on the basis of wedge-shaped webs 38 of the pedal 5 being engaged in correspondingly arranged channels 39 of the pedal 17. The arrangement provides an optimum transmission of torque between the foot support part 5 and the pedal 17.

In order to hold the pedal 17 in a defined neutral position, both with reference to the tiltability around the bearing arrangements 20 and 21 as well as with reference to pivoting around the vertical axis formed by the pin 31 and the bore 33, detent means for providing a defined retaining force is provided and includes special catch elements 40 and 41.

Figure 4:
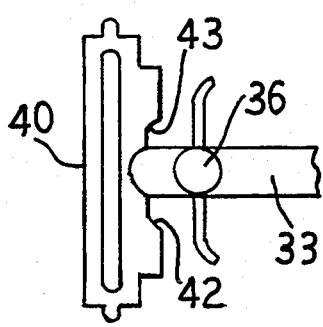
FIG. 4 is a partial plan view illustrating one of the catch arrangements for resisting twisting of the foot switch around a vertical axis.

As illustrated in FIG. 2A and FIG. 4, the catch element 40 serves the purpose of holding the spring beam 33 in the neutral position with a defined retaining force and, after the retaining force or pressure point is overcome, will hold the spring beam in a final position limited by stops 42 and 43 which correspond to the switch positions. FIG. 4 illustrates the relationship of the catch element 40 and the end of the spring beam. The catch element 40 is fashioned as a separate part that can be introduced into the switch plate 16 and is resilient to such an extent as a consequence of its shaping that it requires a certain actuation power to overcome a defined pressure point in the neutral position. The adjustment of the excursion force is intentionally intercepted by the stops or detents 42 and 43 that take effect immediately thereafter, this being a clearly noticeable answerback or feedback for the user for the fact that the corresponding switch element 11 or 12 has been actuated.

Figure 5:
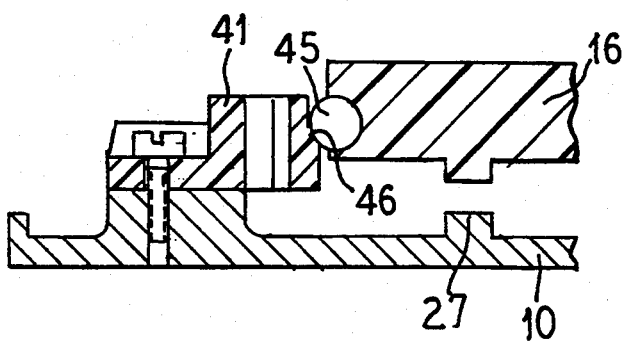
FIG. 5 is a cross sectional view taken approximately along line V—V of FIG. 2B of a catch element for resisting pivoting around a horizontal axis.

The catch element 41 serves the purpose of fixing the switch plate 16 in a neutral position with a defined retaining force and, when this retaining force is overcome, enables the tilting motion until the detent or stop 27 is contacted. Here, too, the path of the adjustment is relatively short and the fact that the detent or stop is reached immediately after overcoming the pressure point is clearly noticeable for the user. This catch element 41 is also resiliently constructed, wherein a cylindrical pin 45 (FIG. 5), which is mounted in the switch plate 16, presses against a slanting surface 46 of the catch element 41. Thus, the switch plate is held in the neutral position with a defined force. After the pressure point is overcome, the switch plate is released in a downward direction until immediately thereafter the switch plate is seated against the detent or stop 27 that, again, corresponds to the switch position.

Although various minor modifications may be suggested by those versed in the art, it should be understood that we wish to embody within the scope of the patent granted hereon all such modifications as reasonably and properly come within the scope of our contribution to the art.

We claim:

1. A foot control mechanism for a dental apparatus comprising a base part having a base plate with a longitudinal axis of symmetry, a plurality of switch control elements being mounted on the base plate, an actuation member containing a switch plate, means for mounting the actuation member on the base plate for tilting movement from a neutral position into at least two switching positions directly opposite one another for triggering a switch/control function of at least one of the plurality of switch control elements, said means for mounting including a pair of spaced apart arrangements, each arrangement including a bearing seat on the base plate receiving a projection of the switch plate to form a bearing for the switch plate to tilt on the base plate, said arrangements being positioned with the bearing seats having their axes extending parallel to one another and transverse relative to the longitudinal axis of symmetry.

2. A foot control mechanism according to claim 1, wherein the switch control elements are arranged in a plane of the bearing seats so that when one of the projections is disposed in one of the bearing seats, an activation element of a switch control element associated with the one bearing seat is depressed.

3. A foot control mechanism according to claim 2, wherein the switch control elements are arranged laterally offset with reference to the longitudinal axis of symmetry of the base plate.

4. A foot control mechanism according to claim 2, wherein both switch positions have a switch element provided with an actuation element allocated to them and both switch elements are arranged with their actuation elements being engaged by the actuation member when the actuation member is in the neutral position.

5. A foot control mechanism according to claim 1, wherein the means for mounting includes a leaf spring, said leaf spring being constructed to resiliently connect the switch plate to the base plate, wherein the leaf spring presses the projections of the arrangements of the switch plate against the bearing seats when the actuation member is in the neutral position.

6. A foot control mechanism according to claim 5, wherein the leaf spring embraces a projection on the base plate and supports a full floating axle mounted in the switch plate.

7. A foot control mechanism according to claim 5, wherein the leaf spring is fashioned as an element that can be easily detached from the base plate.

8. A foot control mechanism according to claim 5, wherein the projection of the base plate has a T-shaped cross section and the leaf spring has end portions for grasping the exposed ends of the T of the projection.

9. A foot control mechanism for a dental apparatus comprising a base part, a plurality of switch control elements being mounted on the base part, an actuation member, means for mounting the actuation member on the base part for movement from a neutral position into at least two switching positions directly opposite one another for triggering a switch/control function of at least one of the plurality of switch control elements, said means for mounting including a pair of arrangements, each arrangement including a bearing seat receiving a projection, said arrangements being positioned with the bearing seats having their axes extending parallel to one another and spaced apart, and detent means for providing a defined retaining force for forming a pressure point which must be overcome to enable the actuation member to be moved from the neutral position, said detent means including a first catch element mounted in the base part engaging an element on the actuation member, said base part having stops for preventing further movement of the actuation member after a short movement from the neutral position.

10. A foot control mechanism according to claim 9, wherein the retaining force of the detent means decreases or becomes ineffective after the pressure point has been overcome and wherein a restoring force, which is lower in comparison to the retaining force, increases and take effect when the stop in the switch position is reached.

11. A foot control mechanism according to claim 9, wherein the actuation member comprises a pedal that is mounted for pivotable movement relative to a switch plate in a horizontal plane around a vertical axis, wherein the switch plate contains a spring beam which interacts, first, with the pedal with the assistance of a dog element received in a slot, said detent means includes a second catch element mounted on the switch plate.

12. A foot control mechanism according to claim 11, wherein the switch plate and the spring beam are constructed as a one-piece part.

13. A foot control mechanism according to claim 12, wherein the one-piece part is a plastic part.

14. A foot control mechanism according to claim 12, wherein the spring beam is fashioned approximately in a T shape with a cross leg, wherein the ends of the cross leg contain actuation surfaces for engaging switch/control elements arranged on the base plate.

15. A foot control mechanism according to claim 11, wherein the second catch element contains stops for limiting the amount of movement of the spring beam from the neutral position.

16. A foot control mechanism according to claim 9, wherein the first and second catch elements are composed of an elastic deformable plastic.

* * * * *